United States Patent [19]
Lin

[11] Patent Number: 4,706,290
[45] Date of Patent: Nov. 10, 1987

[54] METHOD AND APPARATUS EVALUATING AUDITORY DISTORTIONS OF AN AUDIO SYSTEM

[76] Inventor: Hong Yue Lin, No. 490, Chung Shan Road, Sec. 2, Chung Ho, Taipei Hsien, Taiwan

[21] Appl. No.: 772,457

[22] Filed: Sep. 4, 1985

[30] Foreign Application Priority Data

Oct. 12, 1984 [GB] United Kingdom ............... 8425829

[51] Int. Cl.$^4$ .................................................. H04R 29/00
[52] U.S. Cl. ......................................... 381/58; 73/646; 381/98
[58] Field of Search ............... 381/56, 58, 98; 73/646, 73/647, 645, 648

[56] References Cited

U.S. PATENT DOCUMENTS 3,594,506  7/1971  Bauer et al. ............................ 73/646
3,696,206 10/1972  Ida et al. ................................ 73/646
4,307,385 12/1981  Evans et al. ........................... 73/647

Primary Examiner—Forester W. Isen
Attorney, Agent, or Firm—Birch, Stewart, Kolasch & Birch

[57] ABSTRACT

Method and apparatus for evaluating the auditory distortion of an audio system, wherein an audio signal, whose auditory distortions are to be evaluated, is filtered by a notch filter to remove its fundamental frequency, and is then fed through a primary weighting network comprising three high pass filters followed by a secondary weighting network. The filtered, weighted signal is then amplified, recitified, further filtered, compared by taking the ratio with the magnitude of original signal and finally fed to a display unit to sow a figure that represents auditory distortion characteristics consistent with what is actually perceived by human auditory faculties.

10 Claims, 15 Drawing Figures

METHOD AND APPARATUS EVALUATING AUDITORY DISTORTIONS OF AN AUDIO SYSTEM

BACKGROUND OF THE INVENTION

The performance, or quality, of an audio system is generally evaluated in terms of "distortions." However, the "distortions" of an audio system measured by conventional methods such as a "total harmonic distortion", for example, are typically not consistent with actual human auditory perception. It often happens that a listener judges a sound produced by an audio system having greater "total harmonic distortion" to be less distorted than one having less "total harmonic distortion".

The inventor has been studying the relationship between human auditory perception and harmonic distortion for some years and has found that the numerical measurement of distortion that best approximates human auditory perception is obtained by a weighting of the components of harmonic distortion; that is, by a filtered weighting of the high pass filter having 3rd through 4th order and characterised in that the damping factor thereof is (d=2 or quality factor Q=1/d=0.5), the cut off frequency of each order being approximately 12 times the fundamental frequency being measured. Consequently, the main object of the present invention lies in a primary weighting network comprising a high pass filter for the third through the fourth orders, supplemented by a secondary weighting network provided to yield a distortion figure that truly reflects human auditory faculties and which might be named an "auditory distortion parameter".

The apparatus according to this invention also includes a weighting network for the measurement of loudspeaker subharmonics so that the results obtained will best reflect human auditory faculties.

The key index of the performance of a high fidelity stereo system, particularly for a loudspeaker, is audio quality. Yet until now there has not been proposed, nor is there anywhere available, an ideal method of performance evaluation. The quality of a sound, good or bad, has traditionally been represented by the measurement of THD (Total Harmonic Distortion) and/or IMD (Intermodulation Distortion). However, such THD and/or IMD measurements are at best mere physical measurements without any human auditory meaning whatsoever; this is because the sensitivity of human auditory faculties increases in response to the number of "orders" of harmonic components. Thus the traditional methods of measuring the components of each harmonic, without a preliminary weighting process, will unavoidably lead to results that do not conform to human auditory perception, and the figures obtained therefrom will fail to represent the quality of a sound consistent with human auditory perception.

Recognizing the facts set forth above, human auditory perception was studied with the object of developing a rational method for the evaluation of audio distortions consistent with actual human auditory perception. Such a method is the primary object of the present invention.

A further object of this invention is to develop a method for measuring such spurious noises as buzzes or rattles that are inherent in a loudspeaker, and which arise out of deviations, typically those beyond tolerances, in the production procedure, these spurious noises being an essential item on quality control check lists. Traditionally such checking is done by skilled professional workers listening to the sweeping sinusoidal sound waves produced from a loudspeaker. Obviously, however, measurements or evaluations made by an individual listening through bare ears adds a subjective taint to the results, easily making them subject to such dispute that an objective standard cannot be established and automatic measurement operations cannot be instituted. A careful study of spurious noises, now shows them to be attributed to harmonic distortions of higher orders; the present invention is thus the result of thorough research into human auditory perception as related to the orders of harmonics as illustrated in the accompanying drawings, in particular as adapted to the evaluation of spurious noises produced by high fidelity loudspeakers, and fall naturally into the auditory distortion domain disclosed hereunder.

SUMMARY OF THE INVENTION

This invention offers a novel method and apparatus for evaluating the auditory distortion of an audio system, wherein an audio signal, whose auditory distortions are to be evaluated, is filtered by a notch filter to remove its fundamental frequency, and is then fed through a primary weighting network comprising three high pass filters followed by a secondary weighting network. The filtered, weighted signal is then amplified, rectified, further filtered, compared by taking the ratio with the magnitude of original signal and finally fed to a display unit to show a figure that represents auditory distortion characteristics consistent with what is actually perception by human auditory faculties.

BRIEF DESCRIPTION OF THE DRAWINGS

FIG. 15 shows a block diagram of a third embodiment of this invention, illustrating determination of subharmonic components provided as an additional function by a third weighting network that is incorporated into the circuit shown in FIG. 4.

DETAILED DESCRIPTION OF THE INVENTION

The response of human auditory perception to a distortion of sinuoidal waves is normally associated only with the fundamental frequency, but the order of its harmonic components is even more important. Distortions of lower orders of harmonics are less easily detected than distortions for higher orders of harmonics, so the distortions of different orders of a fundamental wave will be detected and perception very differently by the same person.

Figure 1:
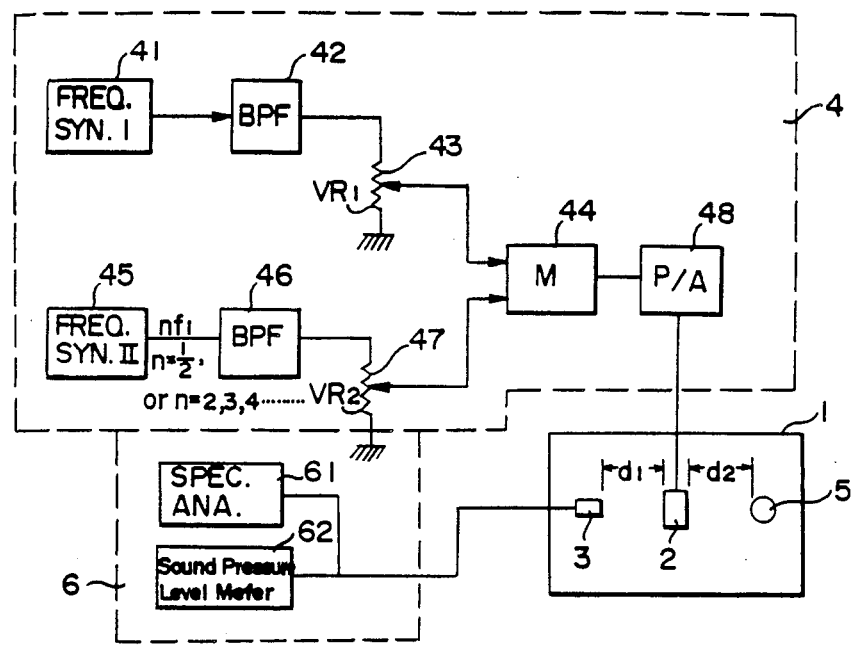
FIG. 1. is a schematic, block diagram showing the arrangement of test equipment employed in experiments conducted to determine the relationship between harmonic components and human auditory perception according to this invention.

To evaluate the amount of distortion of different harmonic orders as detected by human auditory faculties, a series of experiments were performed whose procedure is illustrated in FIG. 1.

In an anechoic chamber 1, as shown in FIG. 1, a loudspeaker 2, rotatable by 180 degrees, is arranged at distance d1 from standard microphone 3. A human tester 5 stands at distance d2 facing loudspeaker 2, the distance d2 being equal to distance d1, which may be 50 cm. Loudspeaker 2 is provided with a harmonic control circuit 4 and standard microphone 3 is provided with sound analyzer 6 including sound pressure level meter 62 and a spectrum analyzer 61, as shown. Harmonic control circuit 4 comprises a first frequency synthesizer 41 connected to a first band pass filter 42 for feeding a signal having a fundamental frequency to a mixer 44 through a first variable resistor VR1, or first volume control 43; and a second frequency synthesizer 45 connected to a second band pass filter 46 for feeding a signal having harmonic frequencies to mixer 44 through a second variable resistor VR2 or second volume control 47. The frequency of the signal as generated by second frequency synethesizer 45 is n times the frequency generated by first frequency synethesizer 41, such a number of harmonic order n can be ½, 2, 3, 4, . . . , where n=½, subharmonic components will be produced; where n=2, 3, 4 or any other integer, harmonic components of higher orders will be produced. A power amplifier 48 is provided to amplify the mixed signal produced by mixer 44, and the mixed, amplified signal is then fed to loudspeaker 2 to produce a sound.

Loudspeaker 2 is first turned to standard microphone 3, with second volume control 47 for harmonic frequencies adjusted to zero and with first volume control 43 for the fundamental frequency adjusted to 90 dB SPL (Sound Pressure Level, 0 dB SPL=0.0002 microbar). Loudspeaker 2 is then tufned towards human tester 5 who starts to adjust second volume control 47 from the zero point in a "louder" direction, until human tester 5 himself can barely begin to perceive a minimal harmonic sound. Thereupon second volume control 47 is set at that point and loudspeaker 2 is again turned to face standard microphone 3, which picks up the sound, including its fundamental and harmonic component, which is then fed to sound analyzer 6 consisting of a spectrum analyzer 61 and a sound pressure level meter 62, so that the contents of the mininal harmonic sound can be measured by spectum analyzer 61. Assuming that the harmonic sound measured is 40 dB SPL (Sound Pressure Level) then the ability of the tester to detect aurally the harmonic of a given order, of a fundamental frequency of the volume corresponding to 90 dB, is expressed as 40−90=−50 dB. Such an ability can be referred to as the threshold of audition, the point at which a sound, typically the minimum sound of a harmonic component, begins to be detected aurally.

Such experiments were conducted with 18 human testers with fundamental frequencies set at 50 Hz, 100 Hz, 200 Hz, 500 Hz, 1 KHz, 1.4 KHz, 2 KHz, 2.8 KHz, 4 KHz, 5.6 KHz, 8 KHz, 11 KHz, 15.6 KHz and 18 KHz while the SPL value was set at 90 dB, with a view to determining the threshold of audition, that is, the threshold of audition of each individual for various harmonics of different orders. Statistics were taken, average calculated, and an analysis given accordingly.

The experiments as described above extended to a subharmonic, characterised by setting n=½ in FIG. 1. It should be pointed out that in the conventional theory of electric circuitry, harmonics of higher orders are all integral multiples of a fundamental frequency, so there should not be a harmonic of the ½ order as such. Such a harmonic of the ½ order, however, does, in fact, exist for a loudspeaker. At certain frequencies, the cone of a loudspeaker may oscillate at a frequency which is half of that of the fundamental frequency, while maintaining the original oscillation of the fundamental frequency. Therefore tests for the threshold of audition, in response to a ½ order harmonic frequency were also made.

The results of the experiments were averaged and summarized on eight curves illustrated in FIGS. 8 through 12 with each curve representing the threshold of audition of each human tester relative to the various differing orders of harmonics under the sound pressure level of 90 dB for each given frequency. For example, in FIG. 8 with the fundamental frequency set at 50 Hz, the threshold of audition to the 7th harmonic was found to be at −53.7 dB, meaning that for a 50 Hz frequency where SPL=90 dB, the level of the 7th harmonic audible to human ear is 90−53.7=36.3 dB SPL (refer to points M, N, and P in FIG. 8).

Figure 8:
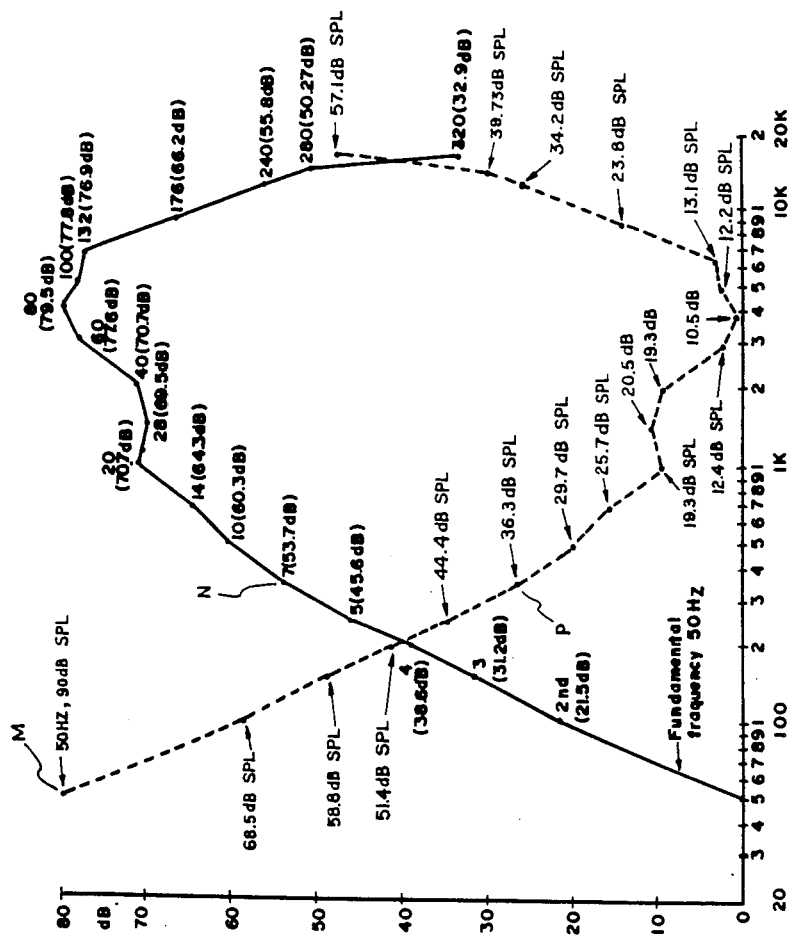
FIG. 8 shows a curve representing an auditory threshold of higher order harmonics having a fundamental frequency of 50 Hz, to be used as a base for the weighting networks employed in the device of this invention. The solid line curve is obtained by inverting a dotted line plotted from the data obtained by the experiment shown in FIG. 1.
Figure 9:
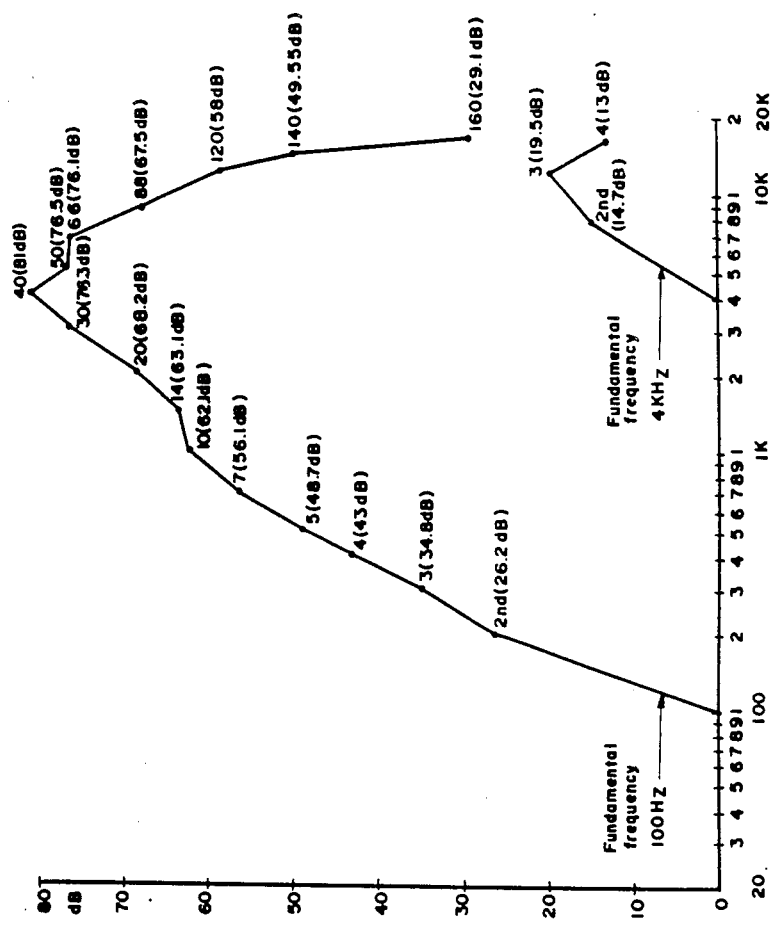
FIGS. 9-12 show various curves similar to the solid line curve shown in FIG. 8, resulting from experiments using different fundamental frequencies such as 100 Hz and 4 KHz (FIG. 9), 200 Hz and 2 KHz (FIG. 10), 500 Hz and 8 KHz (FIG. 11), and 1 KHz (FIG. 12).
Figure 10:
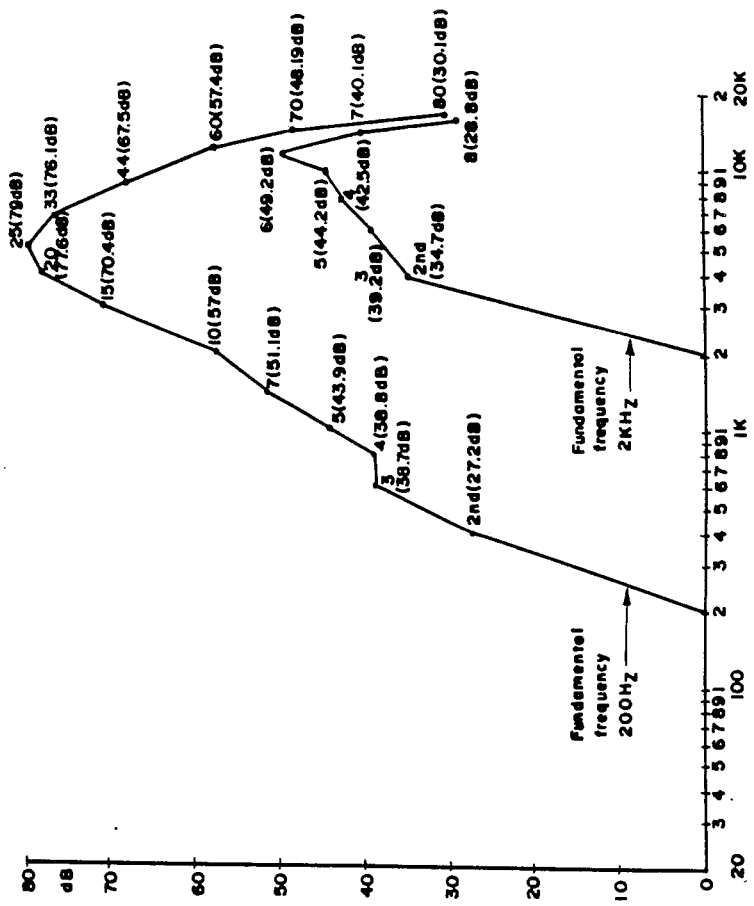
Figure 11:
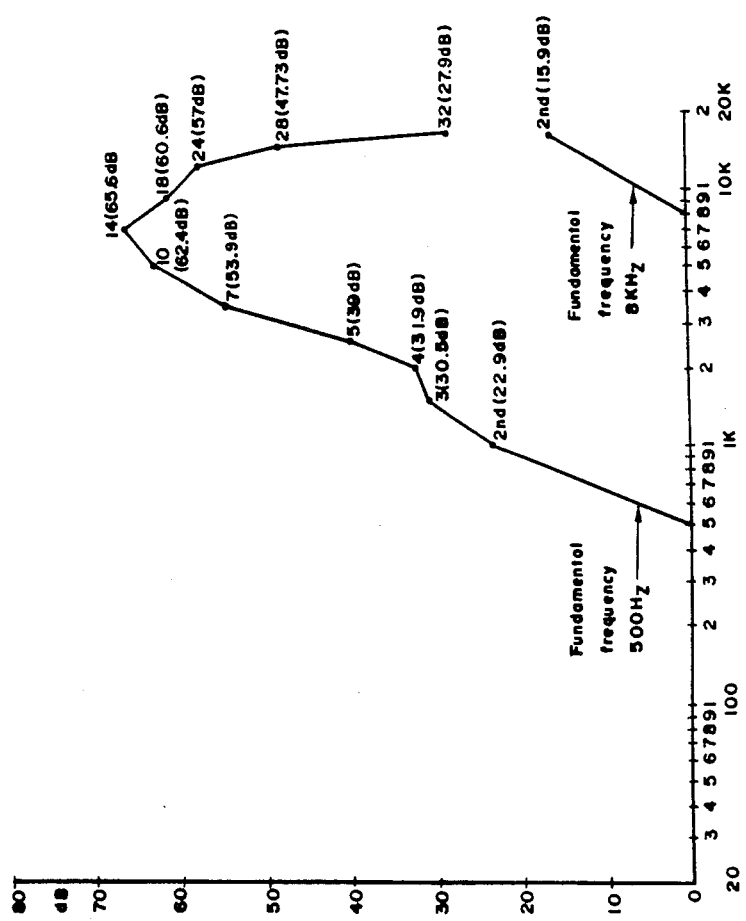
Figure 12:
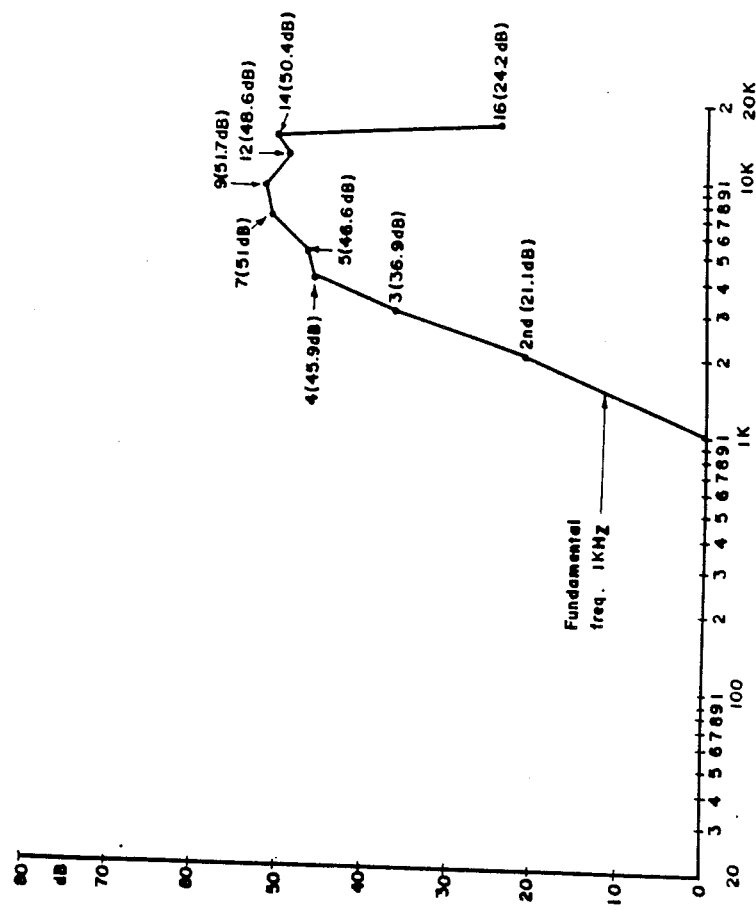

Actually the curves of the threshold of audition as given in FIGS. 8 through 12 should be depicted in a reverse direction, as shown by the dotted line in FIG. 8. The solid line is based on the absolute value obtained from the experiments from which it emerges that by weighting each order of the harmonics with reference to the bold line shown in FIG. 8, being the same for FIGS. 9 through 12, one can obtain a measurement of auditory distortion of a type consistent with human auditory perception on a broad basis.

By consulting the curves shown in FIGS. 8 through 12 with reference to the 70 dB line serving as a reference coordinate (an abscissa, to be exact, to represent 0 dB), it will be seen that it is very close to a Frequency Response Curve produced by the circuit represent by FIG. 2, to be described below.

Figure 2:
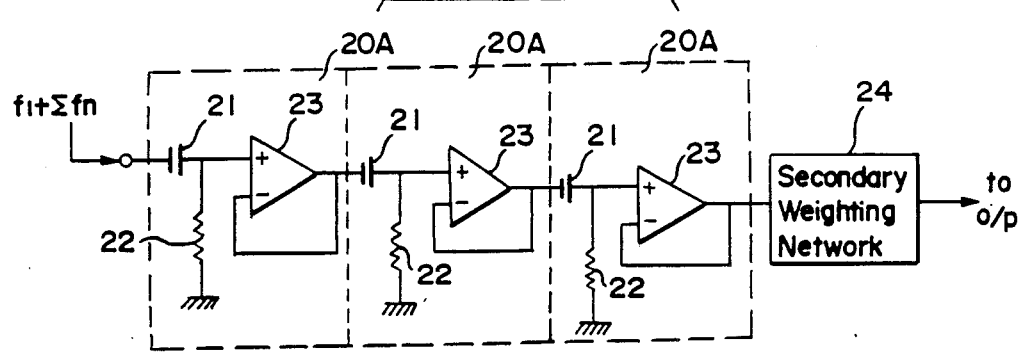
FIG. 2 is a block diagram of an audio circuit that weights the higher order harmonic components of an input signal to produce a distortion figure that truly reflects human auditory faculties.

In FIG. 2 there is shown a circuit which consists of a primary weighting network 20 and a secondary weighting network 24, wherein primary weighting network 20 comprises three high pass filtering units 20A having a filtering circuit composed of a capacitor 21 having a capacitance C and a resistor 22 having a resistance R, and an amplifier 23.

A signal having a frequency $f1 + \Sigma fn$ is applied to the first unit of the three high pass filtering units 20A, 20A, 20A, wherein $$12 f1 = \frac{1}{2\pi RC}$$

OR $$RC = \frac{1}{12} \cdot \frac{1}{2\pi f1}$$

The circuit shown in FIG. 2 makes a composite weighting network having a composite frequency response which closely matches the frequency response shown in FIG. 8 through FIG. 12. For instance, 50 Hz, the frequency response as a composite result of the circuit shown in FIG. 2 should be the same as or very similar to that of the solid line in FIG. 8. The characteristics of each frequency response, as illustrated in FIGS. 8 through FIGS. 12, resembles the characteristics of the band pass filter; thus enabling one to combine one set of high pass filters with another set of low pass filters, to yield the frequency response response characteristics, as shown in FIGS. 8 through FIGS. 12.

The primary weighting network 20 as shown in FIG. 2 therefore essentially consists of the high pass filters mentioned above, while the secondary weighting network 24 in the same illustration is composed of the low pass filters.

The $-3$ dB cutoff frequency for such a low pass filter lies between 2 KHz and 12 KHz, preferably of the range of 4.5 KHz through 6 KHz, the relevant roll-off slope being situated between 18 dB/oct. and 150 dB/oct., preferably at 60 dB/oct.

Figure 6:
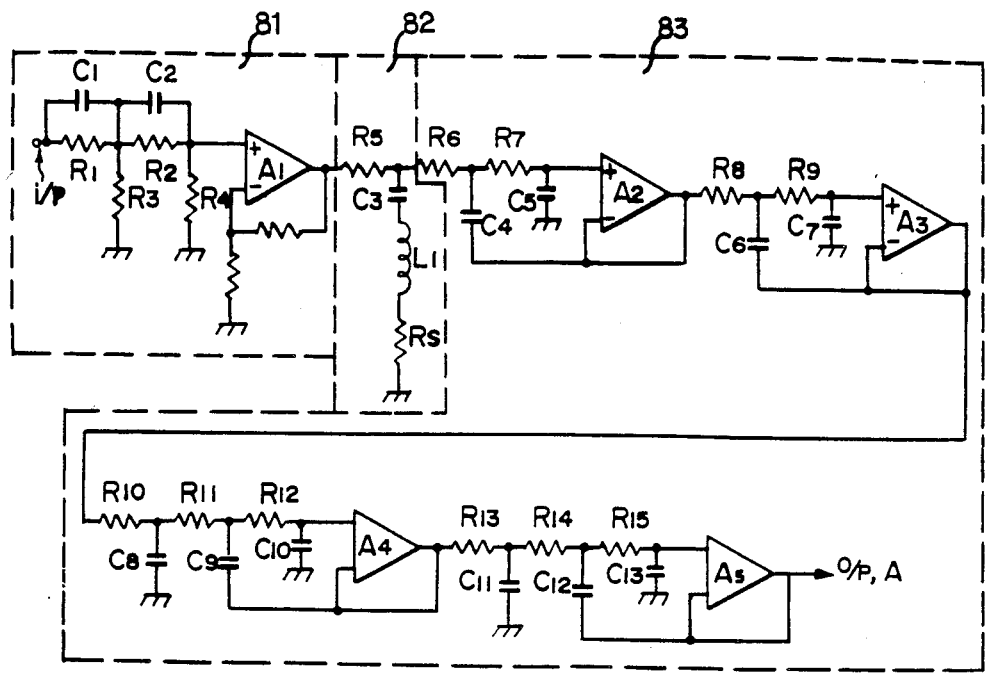
FIG. 6 is a circuit diagram of the secondary weighting network employed in the various embodiments of the device of this invention as shown in FIGS. 4, 5, and 15.
Figure 13:
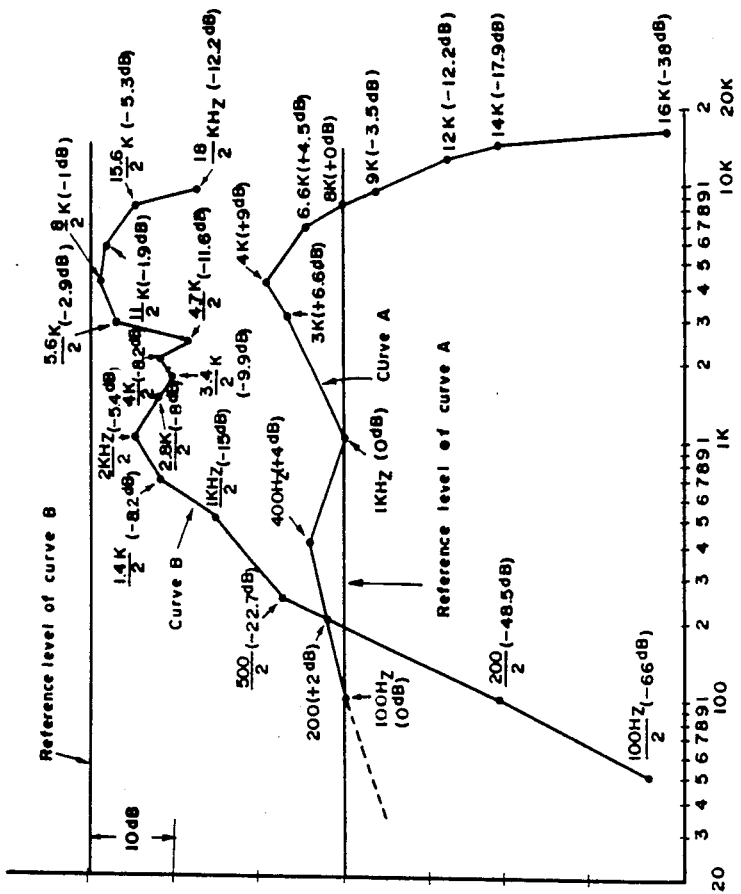
FIG. 13 shows frequency response curve A and curve B, wherein curve A represents the frequency response which should be achieved by the secondary weighting network as covered in the present invention, which, if inverted, is a closematch of the "equal-loudness-level contour"; curve B represents the frequency response which should be achieved by the third weighting network shown in FIG. 15 or FIG. 3.

A careful study of FIGS. 8 through FIGS. 12 shows that close conformity with human auditory perception is obtained when the frequency response characteristics of the secondary weighting network, as illustrated in FIG. 2, is identical to curve A of FIG. 13. The vital point lies in the low pass filter of the secondary weighting network, of which, one embodiment is shown in FIG. 6, whose frequency response corresponds to curve A, of which, the details will be given later.

The secondary weighting network 24 as shown in FIG. 2 has frequency response characteristics resembling the reverse of the equal-loudness-level contours (Robinson D. W. and R. S. Dadson, Br. J. Applied Physics, 1956, Vo. 7, Page 166), like what is shown in Curve A of FIG. 13.

The signals, having been filtered by a circuit exhibited in FIG. 2, will yield an auditory distortion of a magnitude compatible with that of human auditory perception.

Figure 3:
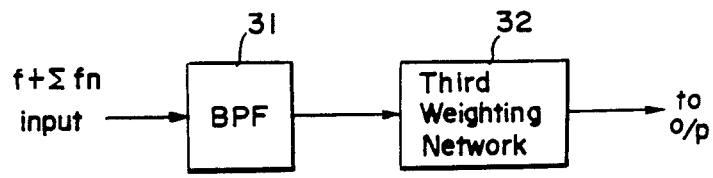
FIG. 3 is a block diagram of an audio circuit for weighting the subharmonic of an input signal to produce a distortion figure a compatible with human auditory faculties.

FIG. 3 shows a circuit comprising a band pass filter (hereinafter as BPF) 31 and a weighting network, 32. This circuit weights the subharmonic component of audio signal to be evaluated.

The fundamental frequency of the signal fed to BPF 31 as shown in FIG. 3 is f1, which contains a subharmonic component with its frequency one half of f1, the resonant frequency of BPF 31 has to be exactly one half of f1 in order that passage will be permitted to those subharmonic components in the input signal, whilst ample attenuation is imposed upon all other frequencies. The subharmonics thus obtained will be weighted by the weighting filter 32, as shown in FIG. 3.

The weighting filter 32 in FIG. 3 comprises at least a low pass filter and a high pass filter. The frequency response characteristics to be expected of Weighting Filter 32 are best represented in Curve B, of FIG. 13.

Curve B, as illustrated in FIG. 13, shows the average outcome of tests taken on 18 individuals with respect to the subharmonic components, and, this is based on the experiments shown in FIG. 1.

In FIG. 1, the fundamental frequency f1 is generated from Frequency Synthesizer 41, with the subharmonic component $\frac{1}{2}$ f1, i.e., $n = \frac{1}{2}$, which is produced by Frequency Synthesizer 45, whereby the threshold of audition, with respect to subharmonic components, illustrated by the 18 individuals who were tested, are obtained by means of the aforementioned methods. The average of the threshold values of the 18 tested individuals, are as follows:

| fundamental freq. (Hz) | 100 | 200 | 500 | 1K | 1.4K |
|---|---|---|---|---|---|
| threshold of audition of subharmonic component refer to the fundamental (dB) | −4 | −21.5 | −47.3 | −55 | −61.8 |
| fundamental freq. (Hz) | 2K | 2.8K | 3.4K | 4K | 4.7K |
| threshold of audition of subharmonic component refer to the fundamental (dB) | −64.6 | −62 | −60.1 | −61.8 | −58.4 |
| fundamental freq. (Hz) | 5.6K | 8K | 11K | 15.6K | 18K |
| threshold of audition of subharmonic component refer to the fundamental (dB) | −67.1 | −69 | −68.1 | −64.7 | −57.8 |

As disclosed hereinbefore, FIG. 8, by reversing the dotted lines representative of the threshold of audition in response to harmonic components of higher orders, one will get the concrete lines given in the same drawing, which rightly represents the characteristics to be demonstrated by the weighting network.

Figure 15:
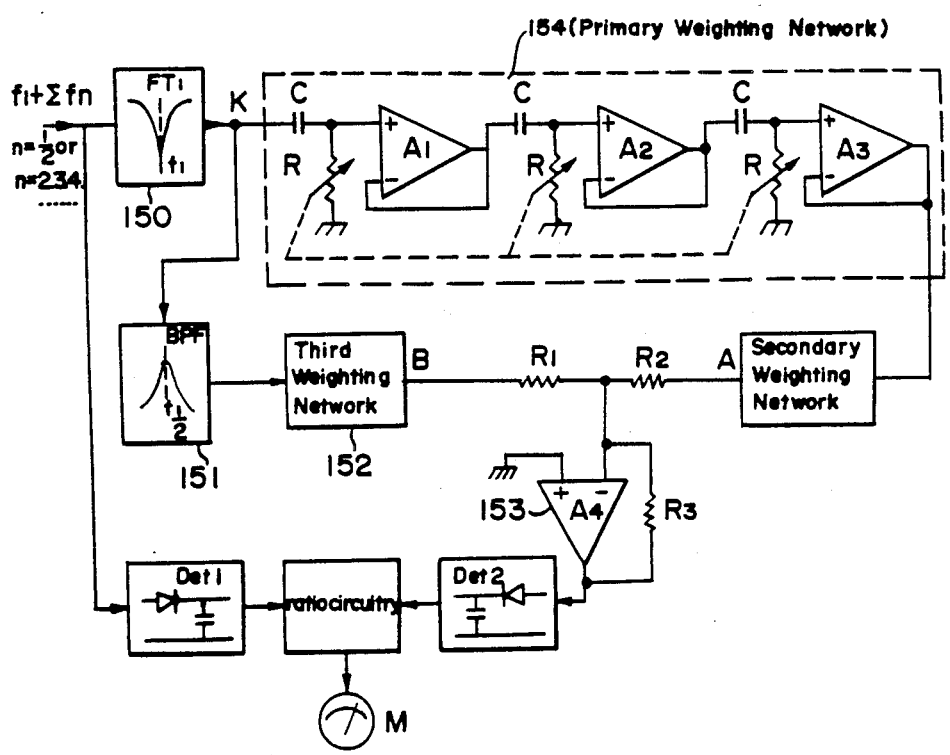
FIG. 15 is achieved using digital processing technique.

Similarly, by a reversal of the threshold of subharmonic components as illustrated in the last Table, that is, by drawing a figure taking the absolute value of the dB values as shown in the last Table, one will get Curve B as shown in FIG. 13, while keeping in mind that the reference level, that is, the 0 dB level line shall have to be shifted upwardly by $+70$ dB, with a view to comply with the presence of the $+70$ dB gain, as illustrated in Example 3, FIG. 15.

It should be pointed out again that distortions measured with conventional distortion meters will by no means reflect the degree or magnitude or modality of distortion appreciated by human auditory faculties. This is because a distortion meter will measure the harmonics regardless of "order", on the same conditions without discrimination whatsoever, and needless to say, without weighting, to the effect that the results obtained through measurement by conventional distortion meters do not bear an acoustic interpretation at all. They, at best, provide for some physical meaning only. It is therefore apparent from the results of the experiments described above, distortions measure by means of the circuit represented by the system of a first embodiment of this invention, as shown in FIG. 4, almost perfectly coincide with human auditory percetion.

EXAMPLE 1

Figure 4:
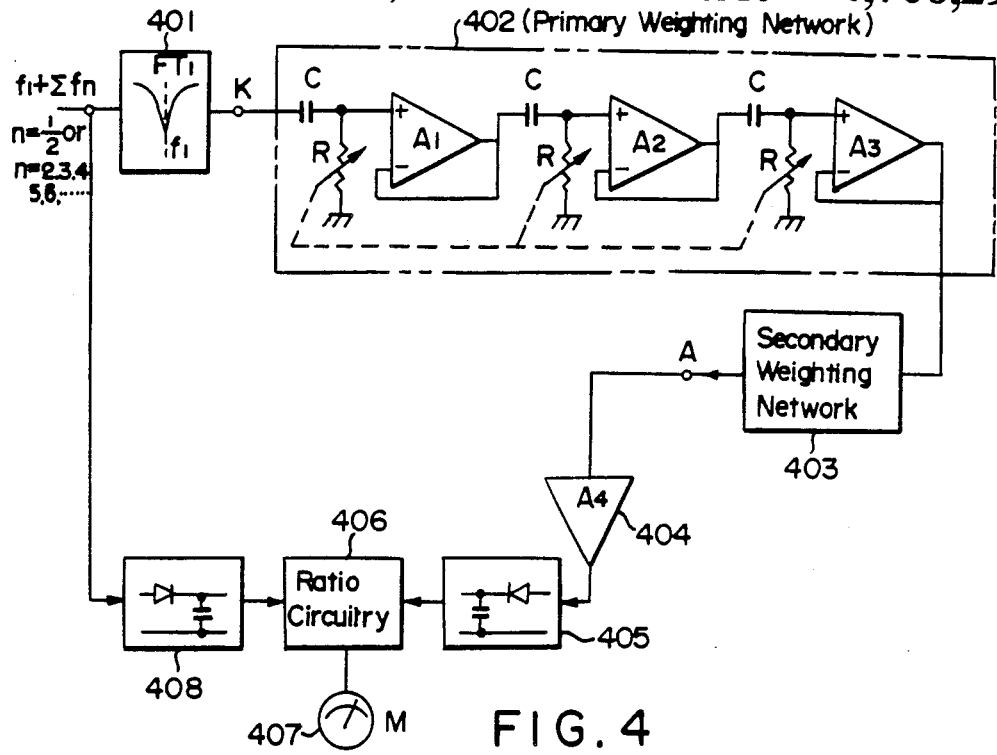
FIG. 4 is a block diagram of a first embodiment of the auditory distortion evaluation device of this invention.

FIG. 4 shows a block diagram of a first embodiment of the auditory distortion evaluation device of this invention. The device comprises a notch filter 401, a primary weighting network 402, a secondary weighting network 403, an amplifier 404, a first rectifier and ripple filter 405, a ratio circuit 406, a display unit (or meter) 407, and a second rectifier and ripple filter 408.

The portion of FIG. 4 from point K to point A represents the circuit as given in FIG. 2, wherein the time constant of any of the three RC filters that constitute the primary weighting network is expressed as $RC = (1/12) \times (\frac{1}{2}\pi f1)$. By derivation, the cutoff frequency of $-3$ dB caused by the value of RC in each segment is $-12$ times the fundamental frequency f1.

The secondary weighting network 403 provides for a characteristic frequency response which is virtually a reversal of the above mentioned equal-loudness-level contours, such as is shown in Curve A of FIG. 13.

Referring to FIG. 4, an input signal $(f1 + \Sigma fn)$ which is to be measured, has its fundamental frequency f1 attenuated at Notch Filter 401, and is output at the output point K, which output signal consists of harmonics alone and is to be weighted for the first time by a primary weighting network, comprising a series of three high pass filters 402, before going to secondary weighting network 403 for a secondary weighting, and then amplified by amplifier 404, rectified by first rectifier 405 for a true r.m.s. AC/DC conversion and further filtered as inputs to the right side terminal of ratio circuitry 406. Such a ratio circuit can be composed of a logarithmic converter, for which the reference input can be considered as the input to the left side terminal of ratio circuity 406, as illustrated in FIG. 4, or else as an input to an analog divider, by considering the input at the left end of ratio circuitry 406, as the denominator and the other input, at the right end thereof, as the numerator.

The input signal $f1 + \Sigma fn$ is also applied to second rectifier 408 whereby the input signal undergoes a true r.m.s. AC/DC conversion and is filtered before being fed to an input point at the left end of ratio circuitry 406.

Ratio circuitry 406 will take the ratio of the two signals fed into the left and the right ends with the results fed to display unit 407 for visual display thereof, which will be a value truly reflective of human auditory perception, in response to audio distortions, and which is to be referred to as "auditory distortion", according to the present invention, which can be expressed in terms of % or dB. The reference value 0 dB of the auditory distortion is defined as follows:

Supposing the frequency response curve of the secondary weighting filter 403 is identical to curve A as shown in FIG. 13, provided that the insertion loss of the notch filter is 0 dB for any frequencies other than for notch frequency f1, and that the weighted and amplified output voltage of amplifier 404 is equal to the voltage of the input signal $f1 + \Sigma fn$, then 0 dB of auditory distortion is obtained when the gain of amplifier 404 is 70 dB. According to the results of numerous experiments conducted by the inventor, the lowest audible level of an auditory distortion, as appreciated by most people, is about 0 to $-10$ dB.

It should to be pointed out that notch filter 401, as shown in FIG. 4, is not absolutely necessary, except when it is desired to determine auditory distortion of a level that is lower than 10 dB, as at such levels, the margin of error will become large.

For the circuit, as illustrated in FIG. 4, if both the primary weighting network and the secondary weighting network 402, 403 are removed, that is, if point K is connected to point A, thereby, removing both weighting filters altogether, then the circuit represented in FIG. 4 would be virtually identical to a conventional THD (Total Harmonic Distortion) Meter; so it would emerge, at once, that a characteristic feature of the present invention would lie in a weighting treatment of the harmonic components.

EXAMPLE 2

Figure 5:
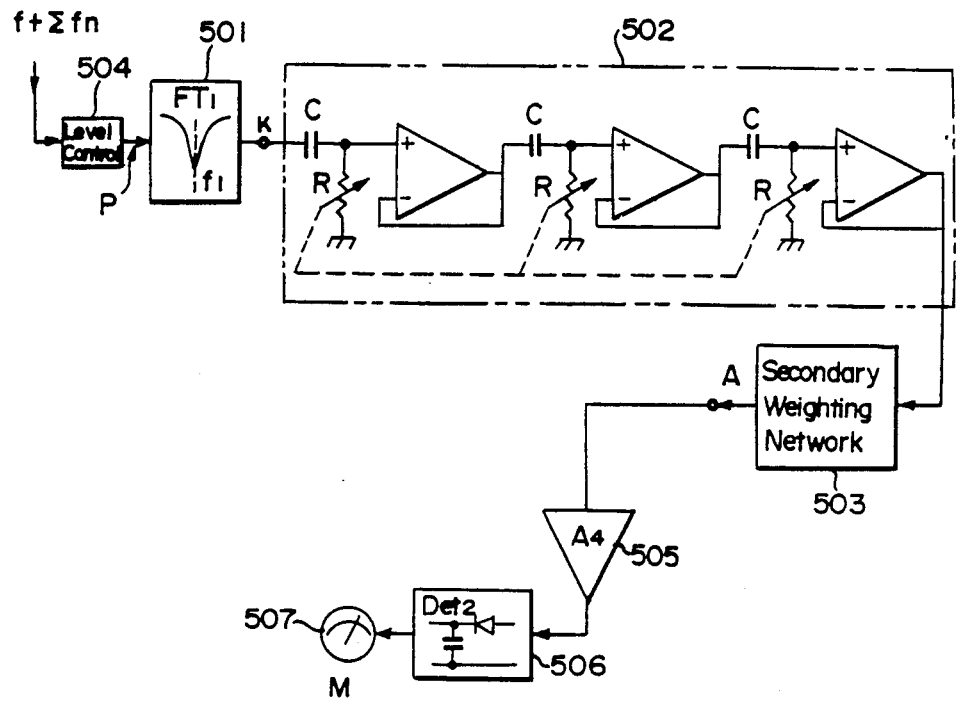
FIG. 5 is a block diagram of a second embodiment of the device of this invention.

FIG. 5 shows a block diagram of a second embodiment of the device of this invention, which comprises a level control circuit 504, a notch filter 501, a primary weighting filter 502, a secondary filter 503, an amplifier 505, a rectifier 506, and a display unit 507.

Level control circuit 504 can be of the manual level control mode or automatic level control mode, both meant to convert the level of the input signal $f1 + \Sigma fn$ into a constant value. The signal voltage at point P would then be a constant value, and, then the rectifier and filter 506 and display unit 507, as shown in FIG. 5, will obtain the same function as do units 408, 405, 406, 407 as shown in FIG. 4 respectively; 402 and 403 shown in FIG. 4, are identical to 502 and 503 shown in FIG. 5; and therefore, as shown in illustrations in FIG. 4 and FIG. 5, will both share like performances, in all respects.

It is advisable to draw % scale or dB scale on the scale plate of the display unit (meter), so as to indicate auditory distortion in terms of percentage or dB readings.

Figure 14:
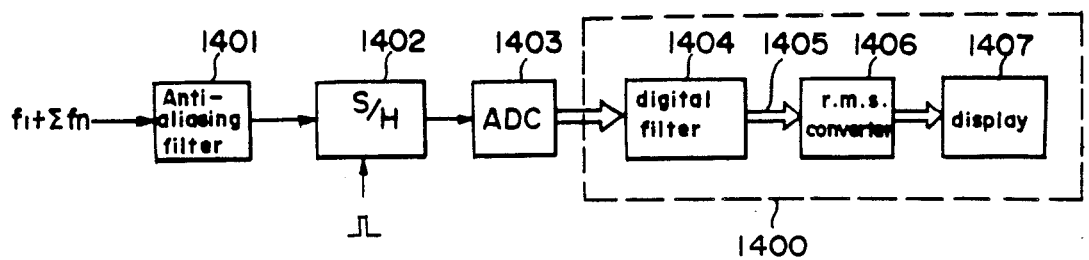
FIG. 14 illustrates a block diagram which shows the circuit performance as shown in FIG. 4 or FIG. 5.

The devices represented in FIG. 4 and FIG. 5 are most noticeably distinguished from conventional distortion meters in the filtering and weighting of harmonic components, The weighting can be accomplished alternatively by the method of digital processing, for which a block diagram is shown in FIG. 14.

The illustrations of FIG. 14 include an anti-aliasing filter 1401, a sample/hold circuit S/H 1402, an analog to digital converter 1403 and a data processing unit 1400 embodying both hardware and software which include digital filter 1404, r.m.s. converter program 1406 and display unit 1407.

The incoming signal $f1 + \Sigma fn$ will go through antialiasing filter 1401, S/H 1402 and ADC 1403 for digitization, to be further subject to treatment by digital filter 1404, that is, weighting processing, to yield a weighted data 1405, prior to being converted by said r.m.s. converter program to yield corresponding r.m.s. value and to be displayed by display unit 1407.

Should the signals to be evaluated be harmonic components of higher orders, then the frequency response from the digital filter 1404, as shown in FIG. 14, shall be identical to a composite frequency response that is a combination of the output from the primary weighting network 20 and the secondary weighting network 24 as shown in FIG. 2, but if the signals to be evaluated contain subharmonic components, then the performance of digital filter 1404 shall correspond to that of BPF 31, as shown in FIG. 3 and get the subharmonic components. Such subharmonic components will be weighted, by means of the frequency response characteristics, as produced from the third weighting network 32 as shown in FIG. 3.

In the circuits illustrated in FIG. 4 and FIG. 5 weighting is imposed on harmonic components of higher orders only, and where determinative measurements of subharmonic components are intended, the circuit disclosed in Example 3 below will have to be employed.

EXAMPLE 3

As described in the foregoing, the circuit, as shown in FIG. 3, serves as a means of weighting the subharmonic component, so by connecting the circuit shown in FIG. 3 to the circuit shown in FIG. 4, one will get a circuit that is capable of determing a subharmonic component, as well as harmonic components of higher orders; an example of this is shown in FIG. 15.

FIG. 15 illustrates a circuit that is entirely identical to that circuit shown in FIG. 4, with the additional incorporation of a band pass filter 151, a third weighting network 152 and a summing amplifier 153.

As a rule, incoming signal $f1 + \Sigma fn$ will have its fundamental frequency $f1$ attenuated by notch filter 150 before being fed to the Band pass filter 151 where only the subharmonic component will be fed through. The resonant frequency of the Band pass filter 151 should be exactly half of $f1$. The subharmonic component will be weighted by weighting filter 152, before being fed to Summing amplifier 153 via R1 for amplification.

The frequency response curve of the weighting filter 152 should be the same as curve B, shown in FIG. 13.

Now suppose that the gain of the band pass filter 151, relative to subharmonic components is taken to be 1, then the gain of the reference level in curve B of FIG. 13 is also 1, in which case $R1 = R2 = R3/3162$, that is, gain of $A4 = 70$ dB, and that is deemed to be a suitable combination, and accordingly, the auditory distortion, determined through the system, represented in FIG. 15 will then correspond totally to actual human auditory perception.

To obtain a reliably accurate measurement result, it is preferable to set the summation of the rejection ratio of both notch filter 150 and band pass filter 151 relative to the fundamental frequency $f1$, individually and severally, to be of a value that is greater than $-80$ dB.

In FIG. 4, FIG. 5 and FIG. 15, the primary weighting network invariably adopted a three-order RC high pass filter arrangement. Nevertheless a four-order or even five-order high pass filter, for instance, can be comprised of cascaded state variable filters, where it is intended to determine spurious noises produced by a loudspeaker, because a loudspeaker will usually suffer ample distortions for harmonics of the second or even third order, especially in frequencies lower than its natural resonant frequency; but, as a matter of fact, distortion of that nature is used to be tolerated by loudspeaker manufacturers, whereas spurious noises, owing to sand or dust that are carried into the gap of a voice coil, are typically of harmonics of higher orders, which would be less tolerable so it has been proposed to employ high pass flters of the fourth or fifth order, with a view to attenuate amply harmonic components of lower orders, while attenuating much less harmonics of higher orders, such a weighting process will prove more suitable for detection of spurious noises produced by loudspeakers than the weighting achieved by the high pass filter of the third order disclosed hereinbefore.

The high pass filters that are employed in the illustrations of FIG. 4, FIG. 5 or FIG. 15 are alike, and all of the RC mode through manual tuning, and employment of a synchronous tracking filter will permit continuous measurement of auditory distortion for the entire audio frequency range, and also a recording of the curve of variation of auditory distortion, by means bf a level recorder, using the frequency as the abscissa.

To reach that objective, the notch filter 150, band pass filter 151 and high pass filter, as illustrated in FIG. 15 must all be of type VCF (Voltage Controlled Filter), a typical instance for the execution of such a VCF is an embodiment using state variable filters, having three outputs each for the high pass filter, low pass filter and the band pass filter respectively; but if the high pass and low pass output are summed together by a summing amplifier, then the output of the summing amplifier will account for a notch filter. In the state variable filter there are incorporated two integrators, each provided with a pair of RC combinations to serve to determine the resonant frequency. It is permissible to replace both resistors in such RC combinations with two analog multipliers to constitute for a voltage controlled filter.

FIG. 6 is one embodiment of the secondary weighting network, as illustrated in FIG. 2, FIG. 4, FIG. 5, or FIG. 15.

The illustration, as shown in FIG. 6, includes a series of high pass filters 81, a band dip filter 82 and a series of low pass filters 83, the most important of which being the low pass filters 83. High pass filter 81 comprises capacitors C1 and C2, resistors R1–R4 and an amplifier A1; and band dip filter 82 comprises resistors R5 and Rs, a capacitor C3, and an inductor L1; and low pass filter 83 comprises resistors R6–R15, capacitors C4 to C13, and amplifiers A2–A5.

The purpose of the circuit, as shown in FIG. 6, is to produce a composite frequency response that will best correspond to the Curve A, as shown in FIG. 13. In Curve A, frequency response for frequencies lower than 4 KHz are achieved by high pass filters 81, whilst the dip in frequency response for frequency ranging from 500 Hz through 3 KHz are achieved through band dip filter 82, and that frequency response for frequencies higher than 4 KHz are achieved through low pass filters 83. From Curve A it will be seen that the frequency response remains free from any substantial variation whatsoever, for frequencies lower than 4 KHz, but will decline sharply, which means a dractic attenuation. Thus it becomes apparent that the roll-off, namely, the sharp declination that is the frequency response for frequencies higher than 4 KHz, deserves much consideration, and the reasons are as follows:

Supposing that the Curve A, as shown in FIG. 13 is revised to be such that the frequency response for frequencies lower than 6.6 KHz turns flat, and that frequency response for frequencies higher than 6.6 KHz remains unchanged, i.e.; as is shown in Curve A FIG. 13, and the secondary weighting network as illustrated in each of FIG. 2, FIG. 4, FIG. 5 or FIG. 15 is replaced by such a network, having the characteristics of such a modified frequency response, the errors arising out of the evaluation of frequencies ranging from 100 Hz through 6.6 KHz would increase by plus/minus 4.5 dB at worst, and that is still permissible in applications.

It is because the low pass filters 83, as shown in FIG. 6, serve to cause roll-offs in the frequency responses for frequencies higher than 4 KHz, so that low pass filters 83 are of prime interest, in the circuit represented in FIG. 6, since if both high pass filter 81 and band dip filter 82 are removed so that low pass filters 83 alone are left, the circuit would only incur an additional tolerance of plus/minus 4.5 dB in the frequency response for frequencies ranging from 100 Hz through 6.6 KHz, as described above.

Thus a prerequisite condition for the secondary weighting network as set forth in the present invention, lies in the incorporation of the low pass filter.

In order to achieve precise results, it is preferable to employ the circuit, as illustrated in FIG. 6, in order to obtain the frequency response exactly as depicted in Curve A of FIG. 13; by doing so, a weighting performance that can best match human auditory perception, will be effected. It should now be apparent that the secondary weighting network, as described above, is adapted for weighting harmonic components of higher orders.

Figure 7:
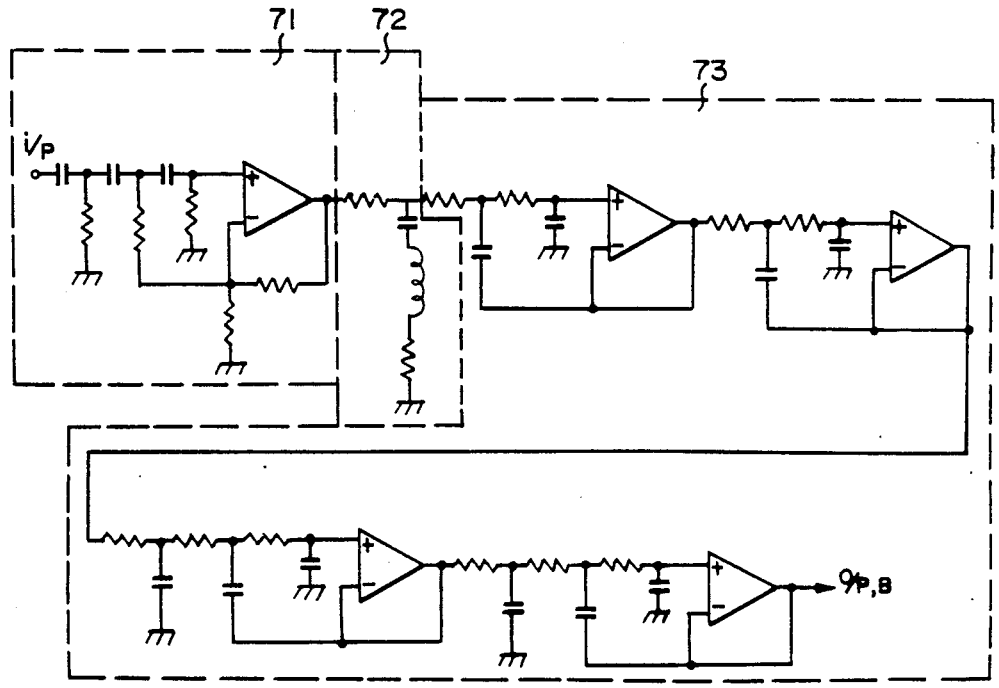
FIG. 7 is a circuit diagram of a third weighting network employed in the embodiments of the device of this invention as shown in FIG. 15 or FIG. 3.

Regarding a third weighting network, serving as a weighting network for subharmonic components exclusively, which is another embodiment provided for according to the invention, is shown in FIG. 7.

As shown in FIG. 7, the third weighting network comprises of a series of high pass filters 71, a band dip filter 72 and a series of low pass filters 73, which, on the whole, resembles very much what is shown in FIG. 6. The frequency response of the circuit, as shown in FIG. 7, must correspond closely to the Curve B, as shown in FIG. 13. For the low pass filters 71, as shown in FIG. 7, the $-3$ dB cutoff frequency lies between 800 Hz and 3 KHz, from which the frequency response for low frequency band, that is, frequencies lower than 1 KHz, as represented in Curve B of FIG. 13, are derived, whereas the Band dip filter 72 serves to produce such a form of frequency response, in which a dip prevails, for frequencies of 1 KHz through 4 KHz, as is shown in Curve B, and that low pass filters 73 are accountable for the frequency response for frequencies higher than 5 KHz, as covered in Curve B; while it has to be stressed that the $-3$ dB cutoff frequency for low pass filters 73 should be somewhere between 3 KHz and 14 KHz.

The band dip filter 72, as seen in FIG. 7, is not absolutely indispensable, if eliminated so that high pass filters 71 and low pass filters 73 remain in the circuit, then the composite frequency response to result therefrom, would be as if resulting from one band pass filter only. That is admittedly less than the precision requirement, but, when carefully designed, the result of a maximum tolerance of plus/minus 5 dB would be obtained, and that will nevertheless be acceptable for usage.

A conclusion, therefore, is that for the third weighting network, as seen in FIG. 7, a necessary prerequisite is the proviso that a series of high pass filters 71, as well as a series of low pass filters 73, are adjoined to make up a series connection.

The device for measuring auditory distortions, according to the present invention, may be used to evaluate preamplifiers, loudspeakers, headphones, power amplifiers, equalizers etc., so as to further improve on the accuracy of the evaluation. The magnitude of the auditory distortion data, measured or evaluated, thereby, will truly serve as an index representative of the amplitudes of distortions, as it is apprehended by human auditory faculties, and is distinguished from conventional approaches, regarding the evaluation of audio distortions, which can only yield results bearing physical meaning, without being representative of the true feelings apprehended by human auditory faculties.

Accordingly, preferred embodiments of the device for evaluating auditory distortions have been described above, by means of example, and it should be understood that the construction and arrangement of the device of this invention can be otherwise modified, by persons skilled in electronics. so that the notch filter shown in FIG. 4 and FIG. 5, may be eliminated. RC-type filters employed in the primary, secondary and third weighting filters may be replaced by digital filters as set forth in the foregoing description, and the amplifier A4 shown in FIG. 4 and FIG. 5 may conveniently be eliminated in certain applications, without departing from the scope and spirit of this invention, as defined in the appended claims.

What is claimed is:

1. A method for evaluating auditory distortions of an audio system, comprising the steps of:
    (a) receiving an input signal containing a fundamental frequency and harmonic components produced by said audio system;
    (b) attenuating said fundamental frequency;
    (c) weighting said harmonic components first with a primary weighting means and then with a secondary weighting means to produce a weighted signal, said primary weighting means comprising a series of high pass filters each one of which having a $-3$dB cutoff frequency proportional to said fundamental frequency, said secondary weighting means comprising a series of low pass filters having a composite $-3$dB cutoff frequency in the range of 2 KHZ to 12 KHZ;
    (d) rectifying and filtering said weighted signal by a first rectifier and a first ripple filter to produce a first signal;
    (e) rectifying and filtering said input signal by a second rectifier and a second ripple filter to produce a second signal;
    (f) comparing the magnitude of said first signal with that of said second signal and displaying the ratio of the magnitudes of said first and second signals.

2. A method for evaluating auditory distortions of an audio system, comprising the steps of:
    (a) applying an input signal containing a fundamental frequency and harmonic components produced by said audio system to a level control circuit to produce a constant level signal containing the fundamental frequency and harmonic components;
    (b) attenuating said fundamental frequency of said constant level signal to produce an attenuated signal;
    (c) weighting said attenuated signal first with a primary weighting means and then with a secondary weighting means to produce a weighted signal, said primary weighting means comprising a series of high pass filters each one of which having a $-3$dB cutoff frequency porportional to said fundamental frequency of said constant level signal, said secondary weighting means comprising a series of low pass filters having a composite $-3$dB cutoff frequency in the range of 2 KHZ to 12 KHZ;
    (d) rectifying and filtering said weighted signal by a rectifier and a ripple filter to produce an output signal; and
    (e) displaying the magnitude of said output signal.

3. A method for evaluating auditory distortions of an audio system, comprising the steps of:

(a) weighting an input audio signal including a subharmonic component, produced by the audio system, first with a primary weighting means comprising a series of high pass filters, and then with a secondary weighting means, to produce a first weighted signal;

(b) applying said input audio signal to a band pass filter to allow only said subharmonic component to pass therethrough and then weighting said subharmonic component by a third weighting means to produce a second weighted signal;

(c) mixing said first weighted signal with said second weighted signal to produce a mixed signal;

(d) rectifying and filtering said mixed signal by a first rectifier and a first ripple filter to produce a first rectified signal;

(e) rectifying and filtering said input audio signal by a second rectifier and a second ripple filter to produce a second rectified signal;

(f) comparing the magnitude of said first rectified signal with that of said second rectified signal and displaying the ratio of the magnitudes of said first rectified signal and said second rectified signal.

4. The method as recited in claim 3 wherein said third weighting means comprises a series of high pass filters and a series of low pass filters connected in series, with said series of high pass filters producing a composite frequency response having a composite −3 dB cutoff frequency ranging from 500 Hz to 3 KHz, and said series of low pass filters producing a composite frequency response having a composite −3 dB cutoff frequency ranging from 3 KHz to 14 KHz.

5. The method as recited in claim 3, wherein said secondary weighting means comprises a series of low pass filters for producing a composite frequency response having a composite −3 dB cutoff frequency in the range of 2 KHz to 12 KHz.

6. An apparatus for evaluating auditory distortions of an audio system, comprising:

primary weighting means for weighting an input audio signal including a subharmonic component produced by the audio system, said primary weighting means including a series of high pass filters;

secondary weighting means for further weighting the weighted signal produced by said primary weighting means;

a band pass filter for filtering said input audio signal to allow only said subharmonic component to pass therethrough to produce a filtered signal;

third weighting means for weighting said filtered signal;

a mixer through which the signals produced by said secondary weighting means and said third weighting means are mixed to produce a mixed signal;

a first rectifier and ripple filter for rectifying and filtering the mixed signal produced by said mixer, to produce a first output signal;

a second rectifier and ripple filter for rectifying and filtering said input audio signal, to produce a second output signal;

ratio circuit means for comparing the magnitudes of said first output signal and said second output signal, to produce a ratio signal; and a display unit for displaying the magnitude of the ratio of said first output signal and second output signal, in response to said ratio signal.

7. The apparatus as recited in claim 6, wherein said third weighting means comprises a series of high pass filters and a series of low pass filters connected in series, said series of high pass filters producing a composite frequency response having a composite −3 dB cutoff frequency ranging from 500 Hz to 3 KHz, and said series of low pass filters producing a composite frequency response having a composite −3 dB cutoff frequency ranging from 3 KHz to 14 KHz.

8. The apparatus as recited in claim 6, wherein said secondary weighting means comprises a series of low pass filters adapted for to producing a composite frequency response having a composite −3 dB cutoff frequency ranging from 2 KHz to 12 KHz.

9. An apparatus for evaluating auditory distortions of an audio system, comprising:

primary weighting means for weighting an input audio signal including a fundamental frequency and harmonic components produced by the audio system, said primary weighting means comprising a series of high pass filters each of which has a −3 dB cutoff frequency proportional to said fundamental frequency;

secondary weighting means for further weighting the weighted signal produced by said primary weighting means, said secondary weighting means comprising a series of low pass filters having a composite −3 dB cutoff frequency in the range of 2 kHz−12 kHz;

a first rectifier and ripple filter for rectifying and filtering said further weighted signal to produce a first output signal;

a second rectifier and ripple filter for rectifying and filtering said input audio signal to produce a second output signal;

ratio circuit means for comparing the magnitudes of said first output signal and said second output signal to produce a ratio signal; and a display unit for showing the magnitude of the ratio of said first output signal and said second output signal, in response to said ratio signal.

10. An apparatus for evaluating auditory distortions of an audio system, comprising:

a level control circuit for maintaining an input audio signal having a fundamental frequency and harmonic components produced by said audio system to become a constant level signal;

an attenuating circuit for attenuating the fundamental frequency of said constant level signal to produce an attenuated signal;

primary weighting means for weighting said attenuated signal, said primary weighting means comprising a series of high pass filters each of which has a −3 dB cutoff frequency proportional to said fundamental frequency;

secondary weighting means for further weighting the weighted signal produced by said primary weighting means, said secondary weighting means includes a series of low pass filters having a composite −3 dB cutoff frequency in the range of 2 kHz−12 kHz;

a rectifier and a ripple filter for rectifying and filtering the further weighted signal to produce an output signal; and a display unit for showing the magnitude of said output signal.

* * * * *